(12) United States Patent
Oh et al.

(10) Patent No.: US 8,003,840 B2
(45) Date of Patent: Aug. 23, 2011

(54) BISMUTH MOLYBDATE-BASED CATALYSTS, METHOD OF PREPARING THEREOF AND METHOD OF PREPARING 1,3-BUTADIENE USING THEREOF

(75) Inventors: Seung Hoon Oh, Daejeon (KR); Seong Jun Lee, Daejeon (KR); Tae Jin Kim, Daejeon (KR); Ahn Seop Choi, Seoul (KR); Young Min Chung, Daejeon (KR); In Kyu Song, Seoul (KR); Ji Chul Jung, Seoul (KR); Hee Soo Kim, Seoul (KR)

(73) Assignees: SK Innovation Co., Ltd., Seoul (KR), part interest; SK Global Chemical Co., Ltd., Seoul (KR), part interest ( * ) Notice: Subject to any disclaimer, the term of this patent is extended or adjusted under 35 U.S.C. 154(b) by 484 days.

(21) Appl. No.: 12/297,352

(22) PCT Filed: Mar. 16, 2007

(86) PCT No.: PCT/KR2007/001308
§ 371 (c)(1),
(2), (4) Date: Oct. 16, 2008

(87) PCT Pub. No.: WO2007/119929
PCT Pub. Date: Oct. 25, 2007

(65) Prior Publication Data
US 2009/0088594 A1  Apr. 2, 2009

(30) Foreign Application Priority Data
Apr. 18, 2006 (KR) .................. 10-2006-0035051

(51) Int. Cl.
*C07C 5/09* (2006.01)
*C07C 5/327* (2006.01)
(52) U.S. Cl. ........ 585/627; 585/629; 585/630; 585/631; 502/305; 502/311
(58) Field of Classification Search .................. None
See application file for complete search history.

(56) References Cited

U.S. PATENT DOCUMENTS

| | | | |
|---|---|---|---|
| 3,764,632 A | 10/1973 | Takenaka et al. | |
| 3,966,823 A | 6/1976 | Takenaka et al. | |
| 3,998,867 A | 12/1976 | Takenaka et al. | |
| 4,322,358 A | 3/1982 | Bither, Jr. et al. | |
| 4,415,482 A | 11/1983 | Ebner | |
| 4,504,692 A | 3/1985 | Arakawa et al. | |
| 4,595,788 A | 6/1986 | Yamamoto et al. | |
| 2003/0162981 A1 | 8/2003 | Kourtakis et al. | |

FOREIGN PATENT DOCUMENTS
WO   WO-9746506   12/1997

OTHER PUBLICATIONS

Cares et al., Ferrite Spinels as Catalysts in the Oxidative Dehydrogenation of Butenes,, Journal of Catalysis 23, pp. 193-203 (1971).
Rennard et al., *Oxidative Dehydrogenation of Butenes over Ferrite Catalysts*, Journal of Catalysis 21, pp. 282-293 (1971).
Bleijenberg et al., Catalytic Oxidation of 1-Butene over Bismuth Molybdate Catalysts, *Journal of Catalysis 4*, pp. 581-585 (1965).
Batist, et al., The Catalytic Oxidation of 1-Butene over Bismuth Molybdate Catalysts, *Journal of Catalysis 5*, pp. 55-64 (1965).
Madeira et al., *Catalytic Oxidate of Dehyrdogenation of n-Butane*, Catalysis Reviews, 44(2), pp. 247-286 (2002).
Toledo et al., *Oxidative Dehydrogenation of 1-butene to Butadiene on $\alpha$-$Fe_2O_3$/$ZNAl_2O_4$ and $ZnFe_xAl_{2-x}O_4$ Catalysts*, Catalysis Letters 30, pp. 279-288 (1995).
Linn et al., Oxidation of 1-Butene over Bismuth Molybdates and Bismuth Iron Molybdate, *Journal of Catalysis*, 41, pp. 134-139 (1976).
Grasselli, R.K., *Ammoxidation*, Handbook of Heterogenous Catalysts, Organic Reactions, vol. 5, pp. 2302-2326.
Welch et al., *Butadiene via Oxidative Dehydrogenation*, Petrochemical Developments, pp. 99-104 (1978).
Grzybowska et al., *The Chemistry of Bi—Mo Oxide Catalysts*, Journal of Catalysis, 25, pp. 25-32 (1972).
Batist et al., *The Catalytic Oxidation of 1-Butene over Bismuth Molybdate Catalysts*, Journal of Catalysis, 12, pp. 45-60 (1968).
Soares et al., *Synergy effects between $\beta$ and $\gamma$ phases of bismuth molybdates in the selective catalytic oxidation of 1-butene*, Applied Catalysis A: General 253 pp. 191-200 (2003).
Bakshi et al., *Catalytic Properties of System $SnO_2$:$Sb_2O_4$ in the Oxidative Dehyrdrogenation of n-Butenes to Butadiene*, vol. 7, p. 177 (1967).
Boutry,et al., Influence of the Degree of Crystallinity and of the Composition on the Activity of $MoO_3$-$Bi_2O_3$ Catalysts, Journal of Catalysis 13, pp. 75-82 (1969).

*Primary Examiner* — Tam M Nguyen
(74) *Attorney, Agent, or Firm* — McDermott Will & Emery LLP (57) ABSTRACT

This invention relates to a bismuth molybdate catalyst, a preparation method thereof, and a method of preparing 1,3-butadiene using the same, and to a bismuth molybdate catalyst, a preparation method thereof, and a method of preparing 1,3-butadiene using the same, in which 1,3-butadiene can be prepared through oxidative dehydrogenation directly using a C4 mixture including n-butene and n-butane as a reactant in the presence of a mixed-phase bismuth molybdate catalyst including $\alpha$-bismuth molybdate (Bi2Mo3On) and $\gamma$-bismuth molybdate (Bi2MoO6). According to this invention, the C4 raffinate, containing many impurities, is used as a reactant, without an additional n-butane separation process, thus obtaining 1,3-butadiene at high yield. Unlike complicated multicomponent-based metal oxides, the catalyst of the invention has simple constituents and synthesis routes, and can be easily formed through physical mixing, and thus is very advantageous in assuring reproducibility and can be directly applied to commercial processes.

10 Claims, 10 Drawing Sheets

BISMUTH MOLYBDATE-BASED CATALYSTS, METHOD OF PREPARING THEREOF AND METHOD OF PREPARING 1,3-BUTADIENE USING THEREOF

CROSS-REFERENCE TO PRIOR APPLICATIONS

This application is a US National Phase Application under 35 USC §371 of International Patent Application No. PCT/KR2007/001308, filed Mar. 16, 2007, which claims priority to and the benefit of Korean Patent Application No. 10-2006-0035051, filed Apr. 18, 2006, each of which are hereby incorporated by reference in their entirety.

TECHNICAL FIELD

The present invention relates, in general, to a bismuth molybdate-based catalyst, a method of preparing the same, and a method of preparing 1,3-butadiene using the same, and, more particularly, to a bismuth molybdate catalyst, a method of preparing the same, and a method of preparing 1,3-butadiene using the same, in which a highly active mixed-phase bismuth molybdate catalyst, comprising single-phase α- and γ-bismuth molybdate catalysts, is prepared, and, in the presence of such a catalyst, high value-added 1,3-butadiene can be prepared using an inexpensive C4 mixture including impurities, such as n-butene and n-butane, without an additional n-butane separation process.

BACKGROUND ART

Generally, methods of preparing 1,3-butadiene for supply to petrochemical markets include steam cracking, the direct dehydrogenation of n-butene, and oxidative dehydrogenation of n-butene. However, since the steam cracking process, which is responsible for 90% or more of the butadiene that is supplied, is not a single process for producing butadiene, it is problematic in that a new naphtha cracker should be introduced to fulfill the increased butadiene demand, and thus the raffinate components, other than butadiene, are further produced. In addition, the direct dehydrogenation of n-butene, which is an endothermic reaction, is unsuitable for use in commercial processes because it requires conditions of high temperature and low pressure for reaction and results in poor thermodynamic properties and very low yields [L. M. Madeira, M. F. Portela, Catal. Rev., vol. 44, p. 247 (2002)].

Hence, the oxidative dehydrogenation of n-butene for producing 1,3-butadiene is regarded as a useful alternative that enables the production of 1,3-butadiene through a single process. In particular, when a C4 raffinate-3 or C4 mixture is used as the source of n-butene, it is advantageous in terms of adding high value to the surplus C4 raffinate components. Specifically, the C4 mixture used as the reactant in the present invention is an inexpensive C4 raffinate remaining after the separation of useful compounds from a C4 mixture produced through naphtha cracking. More specifically, a first mixture remaining after extracting 1,3-butadiene from a C4 mixture produced through naphtha cracking is called raffinate-1, a second mixture remaining after extracting isobutylene from the raffinate-1 is called raffinate-2, and a third mixture remaining after extracting 1-butene from the raffinate-2 is called raffinate-3. Therefore, the C4 raffinate-3 or C4 mixture is composed mainly of 2-butene (trans-2-butene and cis-2-butene), n-butane, and 1-butene.

The oxidative dehydrogenation of n-butene (1-butene, trans-2-butene, cis-2-butene) is a reaction between n-butene and oxygen that produces 1,3-butadiene and water. This reaction is thermodynamically advantageous because stable water is produced as a product, and is also commercially advantageous because the reaction temperature may be decreased. However, in the above reaction using oxygen, many side-reactions, including complete oxidation, etc., are supposed to occur. Thus, there is an urgent need for the development of a catalyst that maximally inhibits such side-reactions and has high selectivity for 1,3-butadiene. The catalysts for use in the oxidative dehydrogenation of n-butene, known to date, include ferrite-based catalysts [J. A. Toledo, M. A. Valenzuela, H. Armendariz, G. Aguilar-Rios, B. Zapzta, A. Montoya, N. Nava, P. Salas, I. Schifter, Catal. Lett., vol. 30, p. 279 (1995)/W. R. Cares, J. W. Hightower, J. Catal., vol. 23, p. 193 (1971)/R. J. Rennard, W. L. Kehi, J. Catal., vol. 21, p. 282 (1971)], tin-based catalysts [Y. M. Bakshi, R. N. Gur'yanova, A. N. Mal'yan, A. I. Gel'bshtein, Petroleum Chemistry U.S.S.R., vol. 7, p. 177 (1967)], bismuth molybdate-based catalysts [A. C. A. M. Bleijenberg, B. C. Lippens, G. C. A. Schuit, J. Catal., vol. 4, p. 581 (1965)]/Ph. A. Batist, B. C. Lippens, G. C. A Schuit, J. Catal., vo.5, p. 55 (1966)]/W. J. Linn, A. W. Sleight, J. Catal., vol. 41, p. 134 (1976)/R. K. Grasselli, Handbook of Heterogeneous Catalysis, vol. 5, p. 2302 (1997)].

Among these catalysts, the bismuth molybdate catalyst is present in various phases, and, in particular, three phases, including α-bismuth molybdate ($Bi_2Mo_3O_{12}$), β-bismuth molybdate ($Bi_2Mo_2O_9$), and γ-bismuth molybdate ($Bi_2MoO_6$), are known to be usable as catalysts [B. Grzybowska, J. Haber, J. Komerek, J. Catal., vol. 25, p. 25 (1972)]. Furthermore, β-bismuth molybdate ($Bi_2Mo_2O_9$) and γ-bismuth molybdate ($Bi_2MoO_6$) are known to have superior activity for the oxidative dehydrogenation of n-butene compared to that of α-bismuth molybdate ($Bi_2Mo_3O_{12}$) [Ph. A. Batist, A. H. W. M. Der Kinderen, Y. Leeuwenburgh, F. A, M. G. Metz, G. C. A. Schuit, J. Catal., vol. 12, p. 45 (1968)/A. P. V. Soares, L. K. Kimitrov, M. C. A. Oliveira, L. Hilaire, M. F. Portela, R. K. Grasselli, Appl. Catal., vol. 253, p. 191 (2003)]. The bismuth molybdate catalyst takes the form of various phases depending on the preparation conditions thereof, and furthermore, upon the preparation of the catalyst, controlling the pH enables the precise control of the phase of the resulting catalyst.

Some patents and literature have reported bismuth molybdate-based catalysts for the oxidative dehydrogenation of n-butene. More specifically, in regard to the production of 1,3-butadiene using pure bismuth molybdate, many reports have been made of the oxidative dehydrogenation of 1-butene at 420° C. using a mixed-phase bismuth molybdate catalyst comprising β-bismuth molybdate and γ-bismuth molybdate, resulting in a maximum yield of 1,3-butadiene of 28.9% [A. P. V. Soares, L. K. Kimitrov, M. C. A. Oliveira, L. Hilaire, M. F. Portela, R. K. Grasselli, Appl. Catal., vol. 253, p. 191 (2003)], of the oxidative dehydrogenation of 1-butene at 415° C. in the presence of each of a β-bismuth molybdate catalyst and a γ-bismuth molybdate catalyst, resulting in the yields of 1,3-butadiene of 51.7% and 56.4%, respectively [P. Boutry, R. Montamal, J. Wrzyszcz, J. Catal., vol. 13, p. 75 (1969)], and of the oxidative dehydrogenation of 1-butene at 422° C. using a β-bismuth molybdate catalyst, resulting in the yield of 1,3-butadiene of 55% [Ph. A. Batist, A. H. W. M. Der Kinderen, Y. Leeuwenburgh, F. A, M. G. Metz, G. C. A. Schuit, J. Catal., vol. 12, p. 45 (1968)].

Moreover, patents related to the preparation of complicated multicomponent-based metal oxide catalysts for use in the preparation of 1,3-butadiene at high yield have been reported [S. Takenaka, A. Iwamoto, U.S. Pat. No. 3,764,632 (1973)/S. Takenaka, H. Shimizu, K. Yamamoto, U.S. Pat. No. 3,966, 823 (1976)/S. Takenaka, H. Shimizu, A. Iwamoto, Y. Kuroda, U.S. Pat. No. 3,998,867 (1976)/M. Arakawa, H. Yoshioka, K. Nakazawa, U.S. Pat. No. 4,504,692 (1985)/H. Yamamoto, K. Okumura, U.S. Pat. No. 4,595,788 (1986)].

The use of the multicomponent-based metal oxide catalyst disclosed in the above literature leads to very high yields of 1,3-butadiene, but is commercially disadvantageous because it is considerably difficult to synthesize the multicomponent-based metal oxide catalyst, and it is also difficult to assure reproducibility. Further, in the case where the C4 mixture is used as a reactant, the constituents of the catalyst are complicated, and thus cause many side-reactions with the components included in the C4 mixture, undesirably greatly changing the catalytic activity and the 1,3-butadiene selectivity.

In addition, one of the problems with the oxidative dehydrogenation of n-butene is that the use of the reactant containing a predetermined amount or more of n-butane results in decreased yields of 1,3-butadiene [L. M. Welch, L. J. croce, H. F. Christmann, Hydrocarbon Processing, p. 131 (1978)]. Thus, in order to overcome the problem occurring when using the C4 mixture as a reactant, the above conventional techniques are limited to the catalytic reaction using only pure n-butene (1-butene or 2-butene) as the reactant. Even in an actual commercial process using a ferrite catalyst, a C4 mixture, in which the amount of n-butane is maintained low, that is, less than 5 wt %, is used as a reactant. As such, in order to use pure n-butene, a process of separating n-butene from the C4 mixture is additionally required, inevitably drastically decreasing economic efficiency.

As mentioned above, the literature or patents related to the catalyst and process for preparing 1,3-butadiene through the oxidative dehydrogenation of n-butene are characterized in that pure 1-butene, 2-butene or a mixture thereof is used as the reactant, or otherwise, a very complicated multicomponent-based metal oxide is used as the catalyst. However, cases in which 1,3-butadiene is prepared using a C4 raffinate, including a high concentration of n-butane-containing C4 raffinate-3 or C4 mixture, as a reactant, in the presence of a mixed-phase bismuth molybdate catalyst comprising single-phase bismuth molybdate catalysts have not yet been reported.

DISCLOSURE

Technical Problem

Accordingly, as a result of continuous studies to overcome the limitations of the conventional techniques, the present inventors have discovered that when a mixed-phase bismuth molybdate catalyst comprising pure single-phase bismuth molybdate catalysts is used, 1,3-butadiene can be prepared through oxidative dehydrogenation using a reactant, that is, an inexpensive C4 mixture including n-butane and n-butene without an additional separation process in the presence of the above catalyst, thus completing the present invention.

Therefore, an object of the present invention is to provide a mixed-phase bismuth molybdate catalyst for use in the preparation of 1,3-butadiene, which is advantageous because it has high activity and simple constituents and synthesis routes and reproducibility can be assured.

Another object of the present invention is to provide a method of preparing the mixed-phase bismuth molybdate catalyst for use in the preparation of 1,3-butadiene.

A further object of the present invention is to provide a method of preparing 1,3-butadiene through oxidative dehydrogenation directly using a C4 mixture as a reactant without an additional separation process in the presence of the above catalyst.

Technical Solution

In order to accomplish the above objects, the present invention provides a bismuth molybdate catalyst for the preparation of 1,3-butadiene, comprising 1 to 40 wt % of α-bismuth molybdate ($Bi_2Mo_3O_{12}$) and 60 to 99 wt % of γ-bismuth molybdate ($Bi_2MoO_6$).

In addition, the present invention provides a method of preparing a bismuth molybdate catalyst for the preparation of 1,3-butadiene, comprising the steps of a) separately dissolving a bismuth precursor and a molybdenum precursor in distilled water according to a ratio of the atomic numbers of bismuth/molybdenum, mixing them together, and then controlling the pH of the mixed solution; b) attaining a solid catalyst from the mixed solution having a controlled pH, and drying the solid catalyst at 70 to 200° C.; c) thermally treating the dried catalyst at 350 to 800° C., thus obtaining an α-bismuth molybdate catalyst; d) obtaining a γ-bismuth molybdate ($Bi_2MoO_6$) catalyst through steps a) to c); and e) mixing 1 to 40 wt % of the α-bismuth molybdate ($Bi_2Mo_3O_{12}$) catalyst and 60 to 99 wt % of the γ-bismuth molybdate ($Bi_2MoO_6$) catalyst.

In addition, the present invention provides a method of preparing 1,3-butadiene, comprising subjecting a reactant including a C4 mixture to oxidative dehydrogenation in the presence of a mixed-phase bismuth molybdate catalyst comprising 1 to 40 wt % of α-bismuth molybdate ($Bi_2Mo_3O_{12}$) and 60 to 99 wt % of γ-bismuth molybdate ($Bi_2MoO_6$), thus preparing 1,3-butadiene.

ADVANTAGEOUS EFFECTS

According to the present invention, a mixed-phase bismuth molybdate catalyst comprising single-phase bismuth molybdate catalysts, which is advantageous because it has high activity and simple constituents and synthesis routes and is able to assure reproducibility, can be obtained. When the bismuth molybdate catalyst of the present invention is used, it is possible to produce 1,3-butadiene through oxidative dehydrogenation directly using a C4 mixture composed mainly of n-butane and n-butene, as a reactant, without an additional n-butane separation process. In particular, even if a C4 mixture including n-butane, having a high concentration of 25 wt % or more, is directly used as a reactant, high activity and 1,3-butadiene selectivity can be attained, and this activity can be maintained for a long period of time.

In the present invention, the C4 mixture or C4 raffinate-3, which is of little usefulness in the petrochemical industry, can be directly applied to the preparation of 1,3-butadiene, thereby assuring a single process for producing 1,3-butadiene and adding high value to the C4 raffinate. Further, a single process for producing 1,3-butadiene is assured, thus meeting the increased 1,3-butadiene demand and actively corresponding to changes in the market demand for 1,3-butadiene.

BEST MODE

Hereinafter, the present invention is described in detail.

As mentioned above, the present invention pertains to a method of preparing a mixed-phase bismuth molybdate catalyst comprising single-phase bismuth molybdate catalysts, active in the oxidative dehydrogenation of n-butene, and of preparing 1,3-butadiene through the oxidative dehydrogenation of n-butene using the prepared catalyst, in which 1,3-butadiene can be prepared using a C4 mixture not subjected to an additional n-butane separation process, as a reactant.

Specifically, in the present invention, the C4 mixture is an inexpensive C4 raffinate composed mainly of n-butane and n-butene remaining after the separation of useful compounds from a C4 mixture produced through naphtha cracking. For example, a first mixture remaining after extracting 1,3-butadiene from the C4 mixture is called raffinate-1, a second mixture remaining after extracting isobutylene from the raffinate-1 is called raffinate-2, and a third mixture remaining after extracting 1-butene from the raffinate-2 is called raffinate-3. Thus, the C4 mixture of the present invention may be a C4 mixture composed mainly of 2-butene (trans-2-butene and cis-2-butene), n-butane, and 1-butene, or C4 raffinate-3, remaining after the separation of the useful components.

The catalyst for the preparation of 1,3-butadiene, which is highly active in the oxidative dehydrogenation of n-butene, is a mixed-phase bismuth molybdate catalyst comprising single-phase α-bismuth molybdate and γ-bismuth molybdate.

The bismuth molybdate catalyst takes the form of various phases depending on the preparation conditions thereof, and thus the catalytic activity thereof varies with the phase. In the present invention, through precise pH control, single-phase bismuth molybdate catalysts are prepared, and furthermore, a mixed-phase bismuth molybdate catalyst comprising single-phase bismuth molybdate catalysts, particularly active in the oxidative dehydrogenation of n-butene, is prepared.

As a bismuth precursor and a molybdenum precursor for the preparation of the bismuth molybdate catalyst, any material may be used as long as it is typically known in the art. For example, the bismuth precursor includes bismuth nitrate, and the molybdenum precursor includes ammonium molybdate.

The bismuth precursor and the molybdenum precursor are separately dissolved in distilled water and are then mixed together. In this case, in order to increase the solubility depending on the type of precursor, an acidic solution (e.g., nitric acid) may be further added. The bismuth precursor and the molybdenum precursor are used in amounts appropriate for the ratio of the atomic number of bismuth/molybdenum depending on the type of single-phase to be prepared. When the precursors are completely dissolved, they are mixed together, and the pH of the solution is controlled. To this end, an ammonia solution may be used, but the present invention is not limited thereto. Thereby, pure single-phase bismuth molybdate catalysts, which vary depending on the mixing ratio of the precursors and the pH condition of the mixture solution, can be obtained.

According to the present invention, for the preparation of α-bismuth molybdate, the amounts of two precursors are adjusted so that the ratio of the atomic number of bismuth/molybdenum is 0.1~2, and preferably, ⅔. When the solutions in which the precursors are dissolved are mixed, the pH is maintained in the range from 0.1 to 5, and preferably 1 to 3. Further, for the preparation of β-bismuth molybdate, the amounts of two precursors are adjusted so that the ratio of the atomic number of bismuth/molybdenum is 0.5~2.5, and preferably, 1. When the solutions in which the precursors are dissolved are mixed, the pH is maintained in the range from 0.1 to 8, and preferably 4 to 6. Furthermore, for the preparation of γ-bismuth molybdate, the amounts of two precursors are adjusted so that the ratio of the atomic number of bismuth/molybdenum is 1~3, and preferably, 2. When the solutions in which the precursors are dissolved are mixed, the pH is maintained in the range from 0.1 to 10, and preferably 1 to 7.

The precursor mixture solution is subjected to pH control depending on the type of single-phase to be prepared, and is then stirred, after which the precipitated solid catalyst solution is filtered through a reduced-pressured filter, thus obtaining a solid sample. The obtained solid sample is dried at 70~200° C., and preferably at 90~150° C., for 24 hours. After the solid catalyst thus produced is placed in an electric furnace, thermal treatment is performed while a temperature of 350° C.~850° C., preferably 400~600° C., and more preferably 450~500° C. is maintained, thereby preparing a pure single-phase bismuth molybdate catalyst.

The pure single-phase bismuth molybdate catalyst thus prepared is α-bismuth molybdate ($Bi_2Mo_3O_{12}$), γ-bismuth molybdate ($Bi_2Mo_2O_9$), or γ-bismuth molybdate ($Bi_2MoO_6$).

According to the present invention, in the oxidative dehydrogenation of n-butene, the reaction takes place in a manner such that the lattice oxygen of the catalyst reacts with two hydrogens of n-butene to thus produce 1,3-butadiene and water, and the lattice oxygen vacancy of the catalyst is filled with molecular oxygen. Therefore, the property of the lattice oxygen of the catalyst affects the reaction activity, and the formed bismuth molybdate catalyst has lattice oxygen properties that vary with the change in the phase. For these reasons, the single-phase bismuth molybdate catalysts prepared in the present invention and the mixed-phase bismuth molybdate catalyst composed of the single-phase catalysts exhibit activities different from each other for the oxidative dehydrogenation of n-butene.

Figure 7:
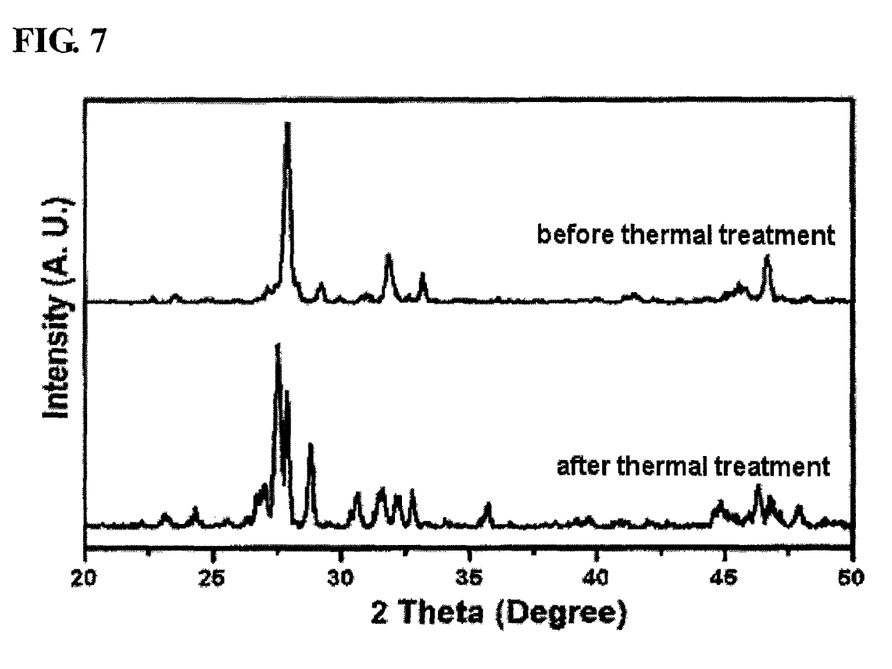
FIG. 7 is a graph showing the results of analysis of X-ray diffraction of the α-bismuth molybdate ($Bi_2Mo_3O_{12}$) catalyst according to the test example of the present invention, before and after thermal treatment (420° C., 72 hours)
Figure 8:
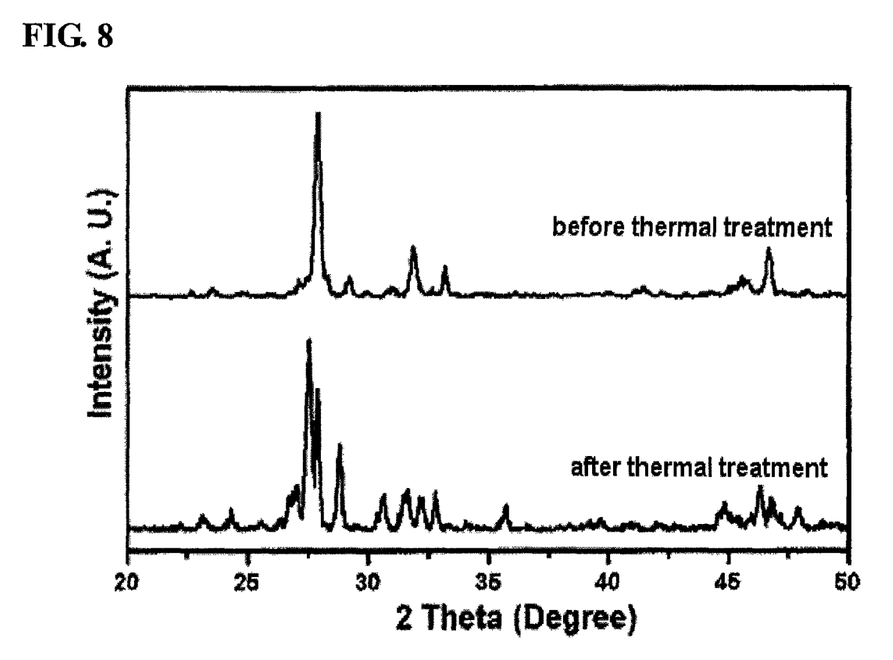
FIG. 8 is a graph showing the results of analysis of X-ray diffraction of the β-bismuth molybdate ($Bi_2Mo_2O_9$) catalyst according to the present invention, before and after thermal treatment (420° C., 72 hours)
Figure 9:
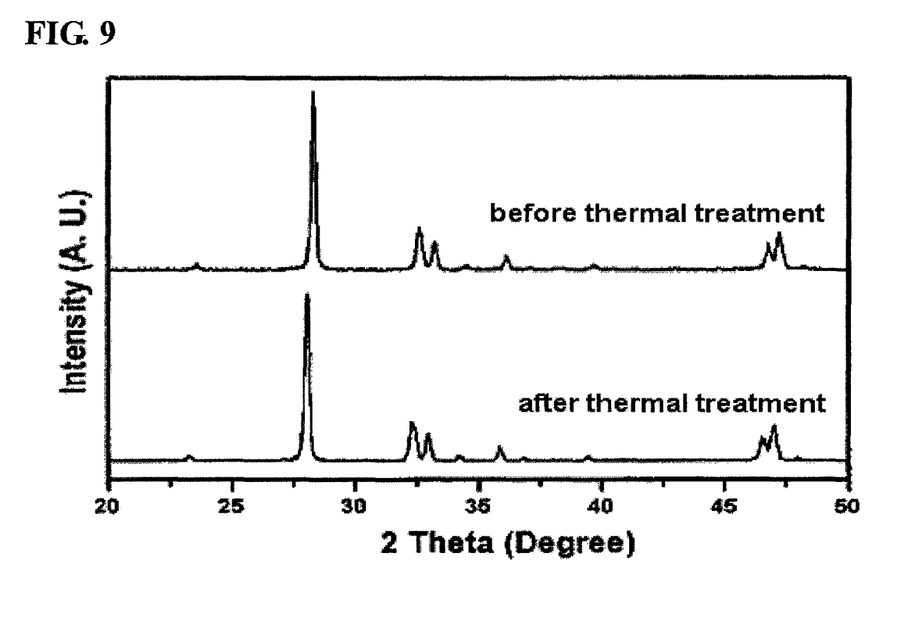
FIG. 9 is a graph showing the results of analysis of X-ray diffraction of the γ-bismuth molybdate ($Bi_2MoO_6$) catalyst according to the present invention, before and after thermal treatment (420° C., 72 hours)

Specifically, according to the test example of the present invention, as the result of comparing the activity of each of the single-phase catalysts, β-bismuth molybdate ($Bi_2Mo_2O_9$) has higher catalytic activity and higher 1,3-butadiene yield than those of α-bismuth molybdate ($Bi_2Mo_3O_{12}$) and γ-bismuth molybdate ($Bi_2MoO_6$), but incurs phase change during the reaction because it is not thermally stable at the high temperature (e.g., 420° C.) at which the oxidative dehydrogenation of n-butene is conducted, and thus is determined to be unsuitable for use as the catalyst of the present invention (FIGS. 7, 8 and 9). Compared to such β-bismuth molybdate ($Bi_2Mo_2O_9$), although α-bismuth molybdate ($Bi_2Mo_3O_{12}$) and γ-bismuth molybdate ($Bi_2MoO_6$) have lower catalytic activity, they have superior thermal stability, and the α-bismuth molybdate ($Bi_2Mo_3O_{12}$) has high adsorptivity to n-butene.

Hence, the catalyst of the present invention, for use in the preparation of 1,3-butadiene, is a mixed-phase bismuth molybdate catalyst in which α-bismuth molybdate ($Bi_2Mo_3O_{12}$) and γ-bismuth molybdate ($Bi_2MoO_6$) are physically mixed at a predetermined ratio. The mixed-phase bismuth molybdate catalyst is composed of 1 to 40 wt %, and preferably 5 to 20 wt %, of α-bismuth molybdate ($Bi_2Mo_3O_{12}$), and 60 to 99 wt %, and preferably 80 to 95 wt %, of γ-bismuth molybdate ($Bi_2MoO_6$), in consideration of the activity thereof. Most preferably, a mixed-phase catalyst comprising 10 wt % of α-bismuth molybdate ($Bi_2Mo_3O_{12}$) and 90 wt % of γ-bismuth molybdate ($Bi_2MoO_6$) is useful.

When the amount of the α-bismuth molybdate ($Bi_2Mo_3O_{12}$) is less than 1 wt %, its adsorptivity to n-butene is decreased and thus the catalytic activity thereof is diminished. On the other hand, when the amount exceeds 40 wt %, the lattice oxygen mobility of the catalyst is deteriorated, and thus the catalytic activity is decreased. Further, if the amount of the γ-bismuth molybdate ($Bi_2MoO_6$) is less than 60 wt %, deteriorated lattice oxygen mobility of the catalyst results, and thus catalytic activity is decreased, whereas if the amount thereof exceeds 99 wt %, decreased adsorptivity to n-butene results, and thus catalytic activity is decreased.

In addition, the present invention provides a method of preparing 1,3-butadiene using a C4 mixture or C4 raffinate-3 not subjected to an additional n-butane separation process, as the source of n-butene, through oxidative dehydrogenation in the presence of the mixed-phase bismuth molybdate catalyst.

According to the embodiment of the present invention, a straight-type Pyrex reactor for a catalytic reaction is mounted in an electrical furnace to maintain the reaction temperature at a predetermined level, and the reactants are allowed to react while continuously passing through the catalytic bed of the reactor.

The reaction is conducted while the reaction temperature is maintained at 300~600° C., preferably 350~500° C., and more preferably 420° C., and the amount of the catalyst is determined so that the gas hourly space velocity (GHSV) is 50~5000 $h^{-1}$, preferably 100~1000 $h^{-1}$, and more preferably 150~500 $h^{-1}$, based on n-butene. The ratio of n-butene:air:steam to be fed as reactants is set to 1:0.5~10:1~50, and preferably 1:3~4:10~30.

In the present invention, the amount of the C4 mixture or C4 raffinate-3, serving as the source of n-butene, and the amount of the air, serving as another reactant, are precisely controlled using a mass flow controller. Further, the steam is supplied into the reactor in a manner such that water in a liquid phase is gasified while being injected using a syringe pump. The temperature of the portion of the reactor where water in a liquid phase is injected is maintained at 150~300° C. and preferably 180~250° C., and thus water to be injected using a syringe pump is instantly gasified into steam, which is then mixed with the other reactants (C4 mixture and air), followed by passing the mixture through the catalytic bed of the reactor.

Among the reactants to be reacted in the presence of the catalyst, the C4 mixture is composed of 0.5 to 50 wt % of n-butane, 40 to 99 wt % of n-butene, and 0.5 to 10 wt % of another C4 mixture. Such another C4 mixture, other than n-butane and n-butene, includes C4 compounds, for example, isobutane, cyclobutane, methylcyclopropane, and isobutene.

When the mixed-phase catalyst composed of the single-phase bismuth molybdates according to the present invention is used, 1,3-butadiene can be produced at high yield through the oxidative dehydrogenation of n-butene using the inexpensive n-butene-containing C4 mixture or C4 raffinate-3 as the reactant. In particular, even if a C4 mixture including n-butane, having a high concentration of 25 wt % or more, is directly used as the reactant, high activity and 1,3-butadiene selectivity can be attained, and the activity can be maintained for a long period of time.

Unlike complicated multicomponent-based metal oxides, the catalyst of the present invention has simple constituents and synthesis routes, and can be easily obtained through physical mixing, and thus is very advantageous in terms of assuring reproducibility, and can also be directly applied to commercial processes without the need for an additional process for separating the reactant because 1,3-butadiene can be obtained at high yield even when the C4 mixture or C4 raffinate-3, containing many impurities, is used as the reactant.

MODE FOR INVENTION

A better understanding of the present invention may be obtained through the following examples which are set forth to illustrate, but are not to be construed as the limit of the present invention.

PREPARATION EXAMPLE 1

<Selection of Precursors and Solvents for Preparing Bismuth Molybdate Catalyst>

As a bismuth precursor, bismuth nitrate ($Bi(NO_3)_3 5H_2O$), and as a molybdenum precursor, ammonium molybdate (($NH_4$)$_6Mo_7O_{24} 4H_2O$) were used. Ammonium molybdate was dissolved in distilled water, whereas bismuth nitrate was dissolved in a strong acidic solution. Thus, bismuth nitrate was dissolved in nitric acid solution-containing distilled water.

While the bismuth nitrate solution was added to the ammonium molybdate solution, an appropriate amount of ammonia solution was further added to control the pH upon precipitation. As such, in order to accurately maintain the desired pH, the bismuth nitrate solution and the ammonia solution were added in droplets to the ammonium molybdate solution. Further, upon precipitation, to obtain a sample having a uniform composition, the solution was thoroughly stirred using a magnetic stirrer.

PREPARATION EXAMPLE 2

<Preparation of Pure-Phase α-Bismuth Molybdate ($Bi_2Mo_3O_{12}$) Catalyst>

In order to prepare pure-phase α-bismuth molybdate, 5.9 g of ammonium molybdate was dissolved in distilled water (60 ml) and was then stirred. Separately, 10.81 g of bismuth nitrate was added to nitric acid-containing distilled water (20 ml), and was then dissolved while being stirred. After the complete dissolution of bismuth was confirmed, the bismuth solution was added in droplets to the molybdate solution. As such, for pH control, a 3 M ammonia solution was added in droplets to adjust the pH to 1.5.

Figure 1:
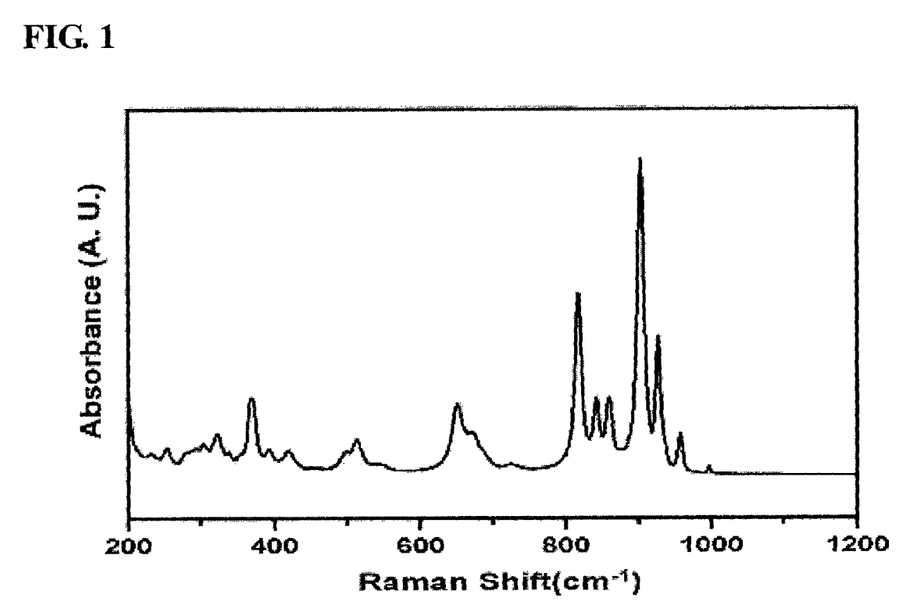
FIG. 1 is a graph showing the results of analysis of Raman spectroscopy of the α-bismuth molybdate ($Bi_2Mo_3O_{12}$) catalyst according to the preparation example of the present invention.
Figure 2:
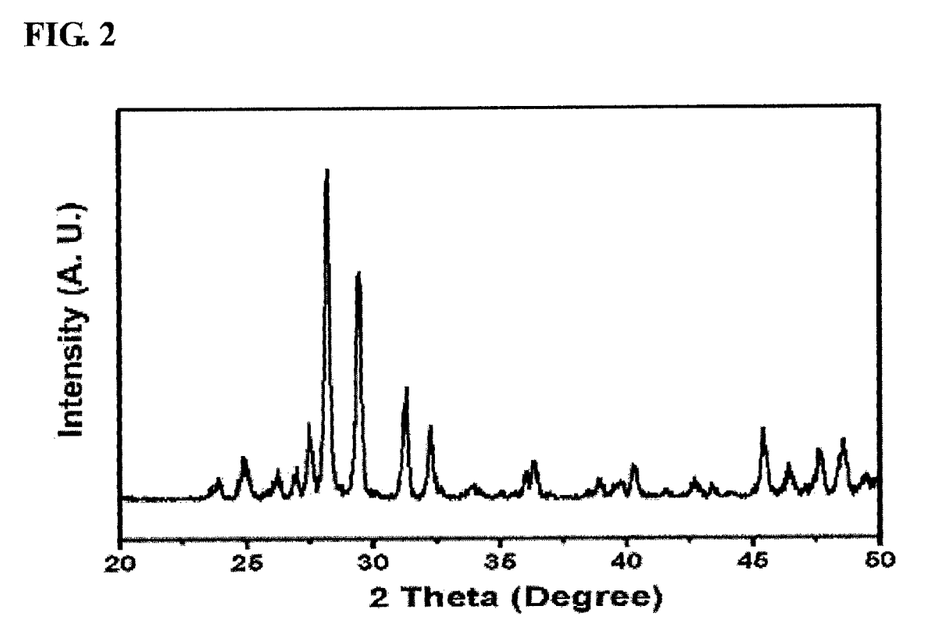
FIG. 2 is a graph showing the results of analysis of X-ray diffraction of the α-bismuth molybdate ($Bi_2Mo_3O_{12}$) catalyst according to the preparation example of the present invention.

The mixture solution thus obtained was stirred at room temperature for 1 hour using a magnetic stirrer, after which the precipitated solution was filtered using a reduced-pressure filter to thus obtain a solid sample, which was then dried at 100° C. for 24 hours. The produced solid catalyst was placed in an electric furnace, and then thermal treatment was performed while a temperature of 475° C. was maintained, thus preparing a pure-phase α-bismuth molybdate ($Bi_2Mo_3O_{12}$) catalyst. The phase of the prepared catalyst was confirmed through Raman spectroscopy and X-ray diffractive analysis. The results are shown in FIGS. 1 and 2.

PREPARATION EXAMPLE 3

<Preparation of Pure-Phase β-Bismuth Molybdate ($Bi_2Mo_2O_9$)Catalyst>

In order to prepare pure-phase β-bismuth molybdate, 4.68 g of ammonium molybdate was dissolved in distilled water (60 ml) and was then stirred. Separately, 12.87 g of bismuth nitrate was added to nitric acid-containing distilled water (20 ml), and was then dissolved while being stirred. After the complete dissolution of bismuth was confirmed, the bismuth solution was added in droplets to the molybdate solution. As such, for pH control, a 3 M ammonia solution was added in droplets to adjust the pH to 5.

This mixture solution was stirred at room temperature for 1 hour using a magnetic stirrer, after which the precipitated solution was filtered using a reduced-pressure filter to thus obtain a solid sample, which was then dried at 100° C. for 24 hours. The produced solid catalyst was placed in an electric furnace, and then thermal treatment was performed while a temperature of 475° C. was maintained, thus preparing a pure-phase α-bismuth molybdate ($Bi_2MO_2O_9$) catalyst, as is desired in the present invention.

Figure 3:
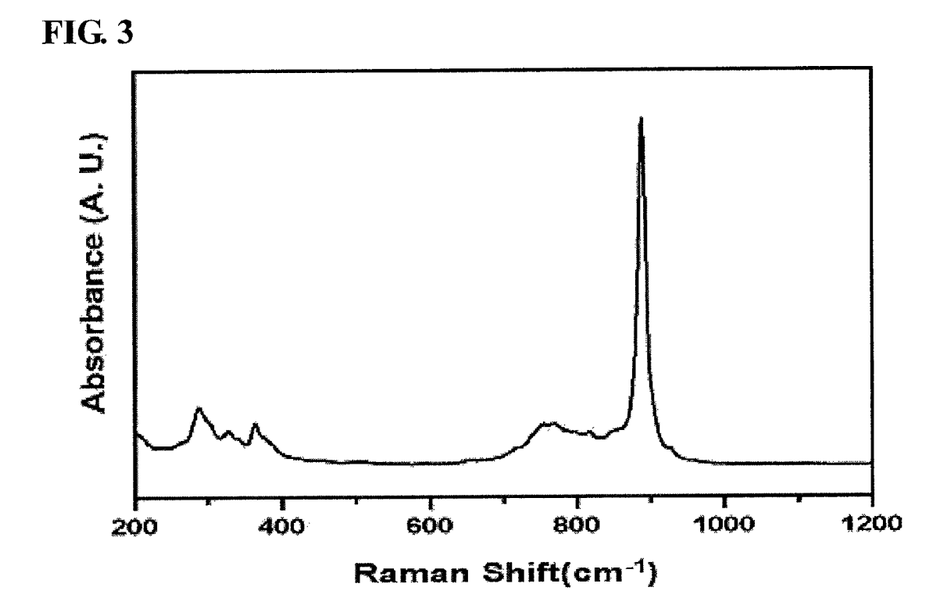
FIG. 3 is a graph showing the results of analysis of Raman spectroscopy of the β-bismuth molybdate ($Bi_2Mo_2O_9$) catalyst according to the preparation example of the present invention.
Figure 4:
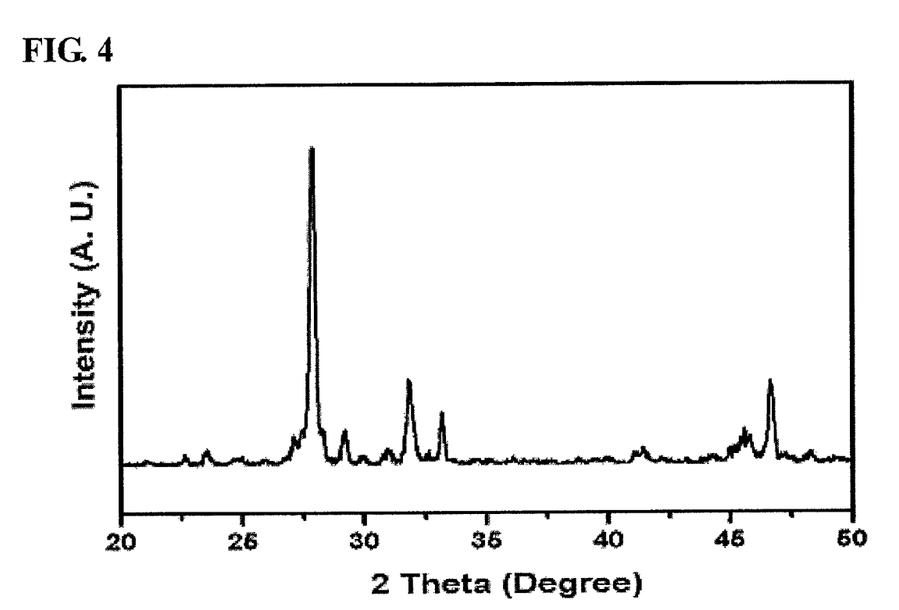
FIG. 4 is a graph showing the results of analysis of X-ray diffraction of the β-bismuth molybdate ($Bi_2Mo_2O_9$) catalyst according to the preparation example of the present invention.

The phase of the prepared catalyst was confirmed through Raman spectroscopy and X-ray diffractive analysis. The results are shown in FIGS. 3 and 4.

PREPARATION EXAMPLE 4

<Preparation of Pure-Phase γ-Bismuth Molybdate ($Bi_2MoO_6$)Catalyst>

In order to prepare pure-phase γ-bismuth molybdate, 2.89 g of ammonium molybdate was dissolved in distilled water (60 ml) and was then stirred. Separately, 15.91 g of bismuth nitrate was added to nitric acid-containing distilled water (20 ml) and was then dissolved while being stirred. After the complete dissolution of bismuth was confirmed, the bismuth solution was added in droplets to the molybdate solution. Further, for pH control, a 3 M ammonia solution was added in droplets. As such, the amount of the ammonia solution was precisely adjusted so that the pH was 1, 2, 3, 4, 5, 6 and 7, resulting in seven samples prepared at the respective pH values.

The mixture solution was stirred at room temperature for 1 hour using a magnetic stirrer, after which the precipitated solution was filtered using a reduced-pressure filter to thus obtain a solid sample, which was then dried at 100° C. for 24 hours. The produced solid catalyst was placed in an electric furnace, and then thermal treatment was conducted while a temperature of 475° C. was maintained, thus preparing seven pure-phase γ-bismuth molybdate ($Bi_2MoO_6$) catalysts, as is desired in the present invention.

Figure 5:
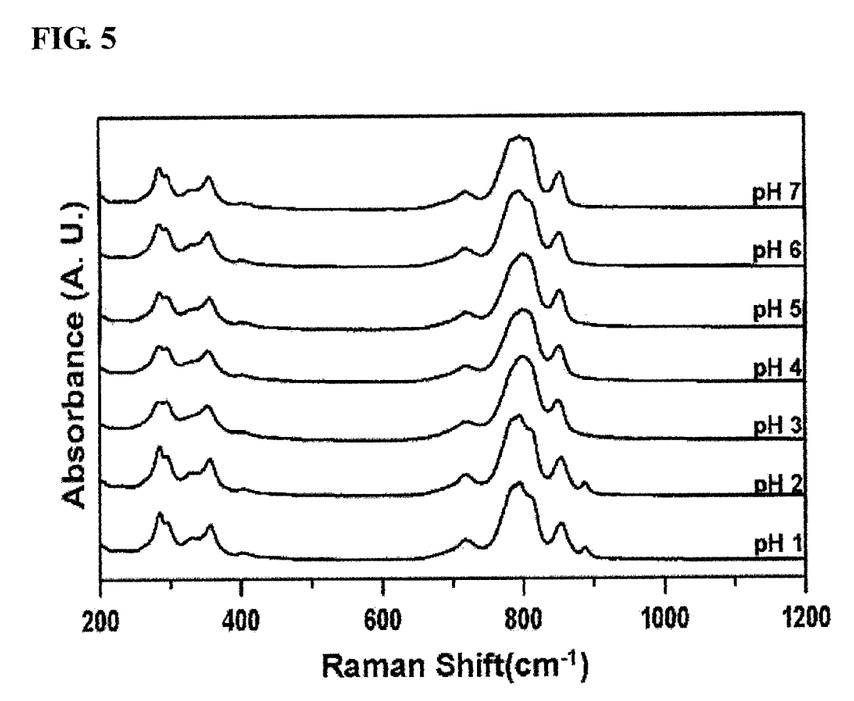
FIG. 5 is a graph showing the results of analysis of Raman spectroscopy of seven γ-bismuth molybdate ($Bi_2MoO_6$) catalysts according to the preparation example of the present invention.
Figure 6:
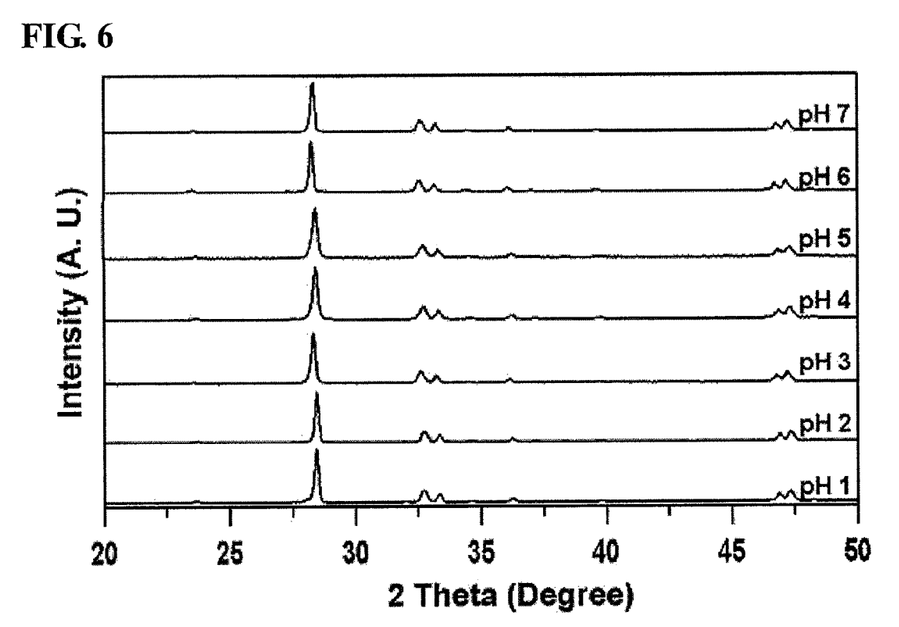
FIG. 6 is a graph showing the results of analysis of X-ray diffraction of seven γ-bismuth molybdate ($Bi_2MoO_6$) catalysts according to the preparation example of the present invention.

The phase of the prepared catalyst was confirmed through Raman spectroscopy and X-ray diffractive analysis. The results are shown in FIGS. 5 and 6. From FIGS. 5 and 6, it was seen that all of the prepared catalysts were γ-bismuth molybdate ($Bi_2MoO_6$), regardless of the pH values.

TEST EXAMPLE 1

<Oxidative Dehydrogenation of C4 Raffinate-3 or C4 Mixture in Presence of Single-Phase Bismuth Molybdate Catalyst>

Using the single-phase bismuth molybdate catalyst of each of Preparation Examples 2, 3 and 4, oxidative dehydrogenation of n-butene was conducted as follows.

As reactants, a C4 mixture, air, and steam were used, and as a reactor, a straight-type Pyrex reactor was used. The composition of the C4 mixture used as the reactant is shown in Table 1 below.

The ratio and GHSV of the reactants were determined based on the n-butene in the C4 mixture. The ratio of n-butene:air:steam was set to 1:3.75:15. The reaction device was designed such that steam was supplied to the inlet of the reactor in the form of water to be directly gasified into steam at 200° C., and was then mixed with the other reactants, that is, the C4 mixture and air, to thus be supplied into the reactor. The amounts of the C4 mixture and air were controlled using a mass flow controller, and the amount of the steam was controlled by adjusting the injection speed of the syringe pump containing water. The reaction temperature was maintained at 475° C.

The amount of the catalyst was adjusted so that the GHSV was 300 $h^{-1}$, based on n-butene. The reaction product was analyzed through gas chromatography. The product was composed of carbon dioxide due to complete oxidation, by-products due to cracking, n-butane, etc., in addition to desired 1,3-butadiene. The conversion of n-butene, the selectivity of 1,3-butadiene, and the yield of 1,3-butadiene were calculated according to Equations 1, 2 and 3 below:

$$\text{Conversion}(\%) = \frac{\text{mol number of reacted } n\text{-butene}}{\text{mol number of fed } n\text{-butene}} \times 100 \quad \text{Equation 1}$$

$$\text{Selectivity}(\%) = \frac{\text{mol number of produced 1,3-butadiene}}{\text{mol number of reacted } n\text{-butene}} \times 100 \quad \text{Equation 2}$$

$$\text{Yield}(\%) = \frac{\text{mol number of produced 1,3-butadiene}}{\text{mol number of fed } n\text{-butene}} \times 100 \quad \text{Equation 3}$$

TABLE 1

Composition of C4 Mixture used as Reactant

| Composition | Molecular Formula | Weight % |
|---|---|---|
| Iso-Butane | $C_4H_{10}$ | 0.011 |
| Normal-Butane | $C_4H_{10}$ | 26.936 |
| Methylcyclopropane | $C_4H_8$ | 0.134 |
| Trans-2-Butene | $C_4H_8$ | 38.341 |
| 1-Butene | $C_4H_8$ | 14.179 |
| Isobutylene | $C_4H_8$ | 0.019 |
| Cis-2-Butene | $C_4H_8$ | 19.971 |
| Cyclopropane | $C_4H_8$ | 0.401 |
| Iso-Pentane | $C_5H_{12}$ | 0.007 |
| Total | | 100 |

TEST EXAMPLE 2

<Reaction Activity of Pure-Phase α-Bismuth Molybdate ($Bi_2Mo_3O_{12}$) Catalyst>

Using the α-bismuth molybdate ($Bi_2Mo_3O_{12}$) catalyst prepared through the preparation method of Preparation Example 2, the reaction test method of Test Example 1 was conducted, thus measuring catalytic activity in the preparation of 1,3-butadiene through the oxidative dehydrogenation of the C4 mixture. The results are shown in Table 2 below.

The pure-phase α-bismuth molybdate ($Bi_2Mo_3O_{12}$) catalyst prepared at a pH of 1.5 had a ratio of Bi/Mo of 0.6, from which the catalyst was determined to have been prepared well. However, the conversion of n-butene was determined to be 13.76%, the selectivity of 1,3-butadiene was determined to be 77.07%, and the yield of 1,3-butadiene was determined to be 10.6%. In consideration thereof, the pure-phase α-bismuth molybdate ($Bi_2Mo_3O_{12}$) catalyst was estimated to exhibit relatively low catalytic activity.

TABLE 2

Reaction Activity of α-Bismuth Molybdate ($Bi_2Mo_3O_{12}$) Catalyst

| Bi/Mo | pH upon Catalyst Preparation | Conversion of n-Butene (%) | Selectivity of 1,3-Butadiene (%) | Yield of 1,3-Butadiene (%) |
|---|---|---|---|---|
| 0.6 | 1.5 | 13.76 | 77.06 | 10.6 |

TEST EXAMPLE 3

<Reaction Activity of Pure-Phase β-Bismuth Molybdate ($Bi_2Mo_2O_9$) Catalyst>

Using the β-bismuth molybdate ($Bi_2Mo_2O_9$) catalyst prepared through the preparation method of Preparation Example 3, the reaction test method of Test Example 1 was conducted, thus measuring catalytic activity in the preparation of 1,3-butadiene through the oxidative dehydrogenation of the C4 mixture. The results are shown in Table 3 below.

The pure-phase β-bismuth molybdate ($Bi_2Mo_2O_9$) catalyst prepared at a pH of 5 had a ratio of Bi/Mo of 0.98, from which the catalyst was determined to have been prepared well. In the catalytic activity test, the conversion of n-butene was determined to be 57.26%, the selectivity of 1,3-butadiene was determined to be 91.83%, and the yield of 1,3-butadiene was determined to be 52.58%. Thus, the pure-phase β-bismuth molybdate ($Bi_2Mo_2O_9$) catalyst was estimated to exhibit excellent catalytic activity.

TABLE 3

Reaction Activity of β-Bismuth Molybdate ($Bi_2Mo_2O_9$) Catalyst

| Bi/Mo | pH upon Catalyst Preparation | Conversion of n-Butene (%) | Selectivity of 1,3-Butadiene (%) | Yield of 1,3-Butadiene (%) |
|---|---|---|---|---|
| 0.98 | 5 | 57.26 | 91.83 | 52.58 |

TEST EXAMPLE 4

<Reaction Activity of Pure-Phase γ-Bismuth Molybdate ($Bi_2MoO_6$) Catalyst>

Using the γ-bismuth molybdate ($Bi_2MoO_6$) catalysts prepared while variously controlling the pH through the preparation method of Preparation Example 4, the reaction test method of Test Example 1 was conducted, thus measuring catalytic activity in the preparation of 1,3-butadiene through the oxidative dehydrogenation of the C4 mixture. The results are shown in Table 4 below.

All of the γ-bismuth molybdate ($Bi_2MoO_6$) catalysts prepared at different pH values had the ratio of Bi/Mo of about 2.0, from which the catalysts were determined to have been prepared well. Among a plurality of γ-bismuth molybdate ($Bi_2MoO_6$) catalysts prepared at different pH values, in the presence of the γ-bismuth molybdate ($Bi_2MoO_6$) catalyst prepared at a pH of 3, the conversion of n-butene was determined to be 50.16%, the selectivity of 1,3-butadiene was determined to be 92.4%, and the yield of 1,3-butadiene was determined to be 46.35%. Thereby, the γ-bismuth molybdate ($Bi_2MoO_6$) catalyst prepared at a pH of 3 was seen to exhibit the best catalytic activity, among the plurality of γ-bismuth molybdate ($Bi_2MoO_6$) catalysts.

46.35%, which was the yield of 1,3-butadiene in the presence of the γ-bismuth molybdate ($Bi_2MoO_6$) catalyst prepared at a pH of 3, was much higher than 10.6% (Example 2), which was the yield of 1,3-butadiene in the presence of the α-bismuth molybdate ($Bi_2Mo_3O_{12}$) catalyst prepared at a pH of 1.5, but was slightly lower than 52.58% (Example 3), which was the yield of 1,3-butadiene in the presence of the β-bismuth molybdate ($Bi_2Mo_2O_9$) catalyst prepared at a pH of 5.

TABLE 4

Reaction Activity of γ-Bismuth Molybdate ($Bi_2MoO_6$) Catalyst

| Bi/Mo | pH upon Catalyst Preparation | Conversion of n-Butene (%) | Selectivity of 1,3-Butadiene (%) | Yield of 1,3-Butadiene (%) |
|---|---|---|---|---|
| 1.88 | 1 | 33.25 | 92.31 | 30.69 |
| 1.94 | 2 | 31.47 | 90.71 | 28.65 |
| 1.96 | 3 | 50.16 | 92.40 | 46.35 |
| 1.95 | 4 | 43.62 | 91.70 | 40.00 |
| 1.94 | 5 | 32.83 | 90.93 | 29.85 |
| 1.95 | 6 | 20.87 | 89.64 | 18.70 |
| 1.97 | 7 | 15.47 | 89.40 | 13.83 |

TEST EXAMPLE 5

<Thermal Stability of α-Bismuth Molybdate ($Bi_2Mo_3O_{12}$) Catalyst>

In order to evaluate the thermal stability of the pure-phase α-bismuth molybdate ($Bi_2Mo_3O_{12}$) catalyst prepared at a pH of 1.5 using the preparation method of Preparation Example 2 and subjected to the reaction test of Test Example 1, the catalyst was thermally treated in an air atmosphere at 420° C. for 72 hours. The results of X-ray diffractive analysis before and after the thermal treatment are shown in FIG. 7.

As shown in FIG. 7, the α-bismuth molybdate catalyst underwent no phase change before or after the thermal treatment, and thus was determined to be structurally stable at the reaction temperature of 420° C. Thereby, the α-bismuth molybdate catalyst could be used as a catalyst structurally stable in the oxidative dehydrogenation of n-butene to be conducted at 420° C.

TEST EXAMPLE 6

<Thermal Stability of β-Bismuth Molybdate ($Bi_2Mo_2O_9$) Catalyst>

In order to evaluate the thermal stability of the pure-phase α-bismuth molybdate ($Bi_2Mo_2O_9$) catalyst, prepared at a pH of 5 using the preparation method of Preparation Example 3 and subjected to the reaction test of Test Example 3, the catalyst was thermally treated in an air atmosphere at 420° C. for 72 hours. The results of X-ray diffractive analysis before and after the thermal treatment are shown in FIG. 8.

As shown in FIG. 8, the β-bismuth molybdate catalyst underwent phase change due to the thermal treatment, and the β-bismuth molybdate catalyst was decomposed into an α-bismuth molybdate catalyst and a 7-bismuth molybdate catalyst by the heat. Therefore, the β-bismuth molybdate catalyst was determined to be structurally unstable in the oxidative dehydrogenation of n-butene to be conducted at 420° C.

Although the pure-phase β-bismuth molybdate catalyst (Example 3) had initial activity superior to the α-bismuth molybdate catalyst (Example 2) and the γ-bismuth molybdate catalyst (Example 4), it had no thermal stability at the reaction temperature of 420° C. and also underwent phase change during the reaction. Thus, the above catalyst could not be used as a catalyst that is efficient for the oxidative dehydrogenation of n-butene, as is desired in the present invention.

TEST EXAMPLE 7

<Thermal Stability of 7-Bismuth Molybdate ($Bi_2MoO_6$) Catalyst>

In order to evaluate the thermal stability of the pure-phase γ-bismuth molybdate ($Bi_2MoO_6$) catalyst, prepared at a pH of 3 using the preparation method of Preparation Example 4 and subjected to the reaction test of Test Example 4, the catalyst was thermally treated in an air atmosphere at 420° C. for 72 hours. The results of X-ray diffractive analysis before and after the thermal treatment are shown in FIG. 9.

As shown in FIG. 9, the γ-bismuth molybdate catalyst underwent no phase change before or after the thermal treatment, and thus was determined to be structurally stable at the reaction temperature of 420° C. Thereby, the 7-bismuth molybdate could be used as a catalyst that was structurally stable in the oxidative dehydrogenation of n-butene to be conducted at 420° C.

EXAMPLE 1

>Preparation of Mixed-Phase Bismuth Molybdate Catalyst>

The pure-phase α-bismuth molybdate ($Bi_2Mo_3O_{12}$) catalyst, prepared at a pH of 1.5 according to Preparation Example 2, and the γ-bismuth molybdate ($Bi_2MoO_6$) catalyst, prepared at a pH of 3 according to Preparation Example 4, were mechanically mixed together. As such, the mixing ratio of α-bismuth molybdate ($Bi_2Mo_3O_{12}$):γ-bismuth molybdate ($Bi_2MoO_6$) was adjusted to 40 wt %:60 wt %, 30 wt %:70 wt %, 20 wt %:80 wt %, 10 wt %:90 wt %, and 5 wt %:95 wt %, thus preparing five mixed-phase bismuth molybdate catalysts.

EXAMPLE 2

<Reaction Activity of Mixed-Phase Bismuth Molybdate Catalyst Comprising α-Bismuth Molybdate ($Bi_2Mo_3O_{12}$) and γ-Bismuth Molybdate ($Bi_2MoO_6$)>

In the presence of the mixed-phase bismuth molybdate catalysts prepared in the mixing ratios of α-bismuth molybdate ($Bi_2Mo_3O_{12}$):γ-bismuth molybdate ($Bi_2MoO_6$) of 40 wt %:60 wt %, 30 wt %:70 wt %, 20 wt %:80 wt %, 10 wt %:90 wt %, and 5 wt %:95 wt % in Example 1, the catalytic activity in the preparation of 1,3-butadiene through the oxidative dehydrogenation of the C4 mixture according to Test Example 1 was measured. The results are shown in Table 5 below.

The selectivity of 1,3-butadiene in the presence of the mixed-phase bismuth molybdate catalyst was increased in proportion to the increase in the amount of the γ-bismuth molybdate ($Bi_2MoO_6$). However, in the presence of the mixed-phase bismuth molybdate catalyst, the conversion of n-butene and the yield of 1,3-butadiene were represented by a volcano-shaped curve with respect to the amount of the γ-bismuth molybdate ($Bi_2MoO_6$) (or the amount of the α-bismuth molybdate ($Bi_2Mo_3O_{12}$)). The five mixed-phase bismuth molybdate catalysts, prepared in Example 1, exhibited the conversion of n-butene and the yield of 1,3-butadiene superior to those of the single-phase α-bismuth molybdate ($Bi_2Mo_3O_{12}$) and γ-bismuth molybdate ($Bi_2MoO_6$).

Among the five mixed-phase bismuth molybdate catalysts, in the presence of the mixed-phase bismuth molybdate catalyst having the mixing ratio of α-bismuth molybdate ($Bi_2Mo_3O_{12}$):γ-bismuth molybdate ($Bi_2MoO_6$) of 10 wt %:90 wt %, the conversion of n-butene was determined to be 65.72%, and the yield of 1,3-butadiene was determined to be 60.13%, thus having the highest catalytic activity. In particular, in the presence of the mixed-phase bismuth molybdate catalyst having the mixing ratio of α-bismuth molybdate ($Bi_2Mo_3O_{12}$):γ-bismuth molybdate ($Bi_2MoO_6$) of 10 wt %:90 wt %, the yield of 1,3-butadiene was higher than the yield (52.58%) of 1,3-butadiene in the presence of the pure-phase α-bismuth molybdate ($Bi_2Mo_2O_9$) prepared at a pH of 5 in Preparation Example 3. Thereby, the above catalyst was seen to exhibit maximum catalytic activity among the plurality of catalysts prepared in the present invention.

The γ-bismuth molybdate ($Bi_2MoO_6$) was known to have a diffusion coefficient of lattice oxygen larger than that of the α-bismuth molybdate ($Bi_2Mo_3O_{12}$), and thus to exhibit excellent lattice oxygen mobility, and further, the α-bismuth molybdate ($Bi_2Mo_3O_{12}$) was known to have adsorptivity to n-butene, serving as a reactant, superior to that of the γ-bismuth molybdate ($Bi_2MoO_6$). Therefore, the high catalytic activity of the mixed-phase bismuth molybdate catalyst composed of α-bismuth molybdate ($Bi_2Mo_3O_{12}$) and γ-bismuth molybdate ($Bi_2MoO_6$) is considered to be due to synergic effects related to the advantages of the individual catalyst phases (larger lattice oxygen diffusion coefficient of γ-bismuth molybdate ($Bi_2MoO_6$) and high adsorptivity of α-bismuth molybdate ($Bi_2Mo_3O_{12}$) to n-butene).

TABLE 5

Reaction Activity of Mixed-Phase Bismuth Molybdate Catalyst including α-Bismuth Molybdate ($Bi_2Mo_3O_{12}$) and γ-Bismuth Molybdate ($Bi_2MoO_6$)

| α-$Bi_2Mo_3O_{12}$ (wt %) | γ-$Bi_2MoO_6$ (wt %) | Conversion of n-Butene (%) | Selectivity of 1,3-Butadiene (%) | Yield of 1,3-Butadiene (%) |
|---|---|---|---|---|
| 100 | 0 | 13.76 | 77.06 | 10.60 |
| 40 | 60 | 54.41 | 91.47 | 49.77 |
| 30 | 70 | 58.61 | 89.62 | 52.52 |
| 20 | 80 | 61.22 | 90.64 | 55.49 |
| 10 | 90 | 65.72 | 91.50 | 60.13 |
| 5 | 95 | 60.31 | 92.55 | 55.81 |
| 0 | 100 | 50.16 | 92.40 | 46.35 |

EXAMPLE 3

Oxidative Dehydrogenation of n-Butene depending on Reaction Time

Figure 10:
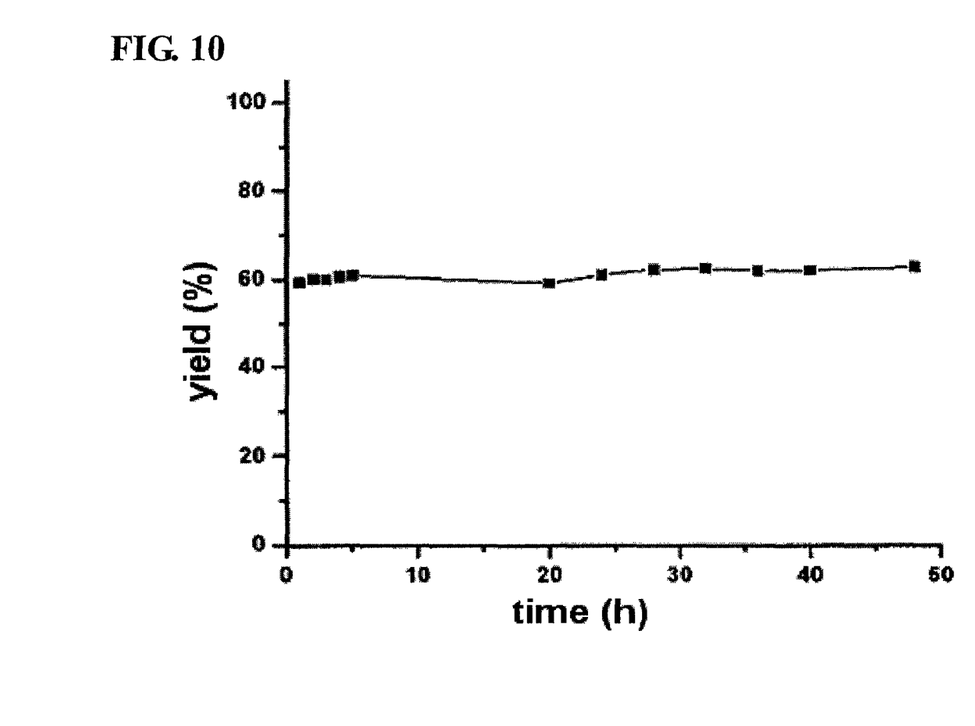
FIG. 10 is a graph showing changes in the yield of 1,3-butadiene depending on reaction time in the presence of a mixed-phase bismuth molybdate catalyst comprising α-bismuth molybdate ($Bi_2Mo_3O_{12}$):γ-bismuth molybdate ($Bi_2MoO_6$) at a mixing ratio of 10 wt %:90 wt %, according to the example of the present invention.

In order to evaluate the degree of catalytic inactivity, using the catalyst having the mixing ratio of α-bismuth molybdate ($Bi_2Mo_3O_{12}$):γ-bismuth molybdate ($Bi_2MoO_6$) of 10 wt %:90 wt %, prepared in Example 1 and exhibiting the highest catalytic activity in Test Example 5, changes in the yield of 1,3-butadiene through the oxidative dehydrogenation of the C4 mixture of Example 1 depending on the reaction time were measured. The results are shown in FIG. 10. As shown in FIG. 10, the above catalyst had almost no catalytic inactivity for 48 hours after the initiation of the reaction, and the activity thereof was continuously maintained at a high level. Therefore, the catalyst prepared in the present invention was determined to be very efficient for the oxidative dehydrogenation of n-butene.

The invention claimed is:

1. A mixed-phase bismuth molybdate catalyst for preparation of 1,3-butadiene, comprising 1 to 40 wt % of α-bismuth molybdate ($Bi_2Mo_3O_{12}$) and 60 to 99 wt % of γ-bismuth molybdate ($Bi_2MoO_6$).

2. A method of preparing 1,3-butadiene, comprising subjecting a reactant including a C4 mixture to oxidative dehydrogenation in a presence of a mixed-phase bismuth molybdate catalyst comprising 1 to 40 wt % of α-bismuth molybdate ($Bi_2Mo_3O_{12}$) and 60 to 99 wt % of γ-bismuth molybdate ($Bi_2MoO_6$), thus preparing 1,3-butadiene.

3. The method according to claim 2, wherein the reactant comprises a C4 mixture including n-butane and n-butene, air, and steam.

4. The method according to claim 2, wherein the C4 mixture comprises 0.5 to 50 wt % of n-butane, 40 to 99 wt % of n-butene, and 0.5 to 10 wt % of another C4 mixture.

5. The method according to claim 3, wherein the reactant comprises n-butene:air:steam at a ratio of 1:0.5~10:1~50.

6. The method according to claim 2, wherein the oxidative dehydrogenation is conducted at a reaction temperature of 300~600° C. and a gas hourly space velocity of 50~2000 $h^{-1}$.

7. A method of preparing a mixed-phase bismuth molybdate catalyst for preparation of 1,3-butadiene, comprising steps of:
 a) separately dissolving a bismuth precursor and a molybdenum precursor in distilled water according to a ratio of atomic number of bismuth/molybdenum, mixing them together, and then controlling a pH of the mixed solution;
 b) attaining a solid catalyst from the mixed solution having a controlled pH, and then drying the solid catalyst at 70 to 200° C.;
 c) thermally treating the dried catalyst at 350 to 800° C., thus obtaining an α-bismuth molybdate catalyst;
 d) obtaining a γ-bismuth molybdate ($Bi_2MoO_6$) catalyst through steps a) to c); and
 e) mixing 1 to 40 wt % of the α-bismuth molybdate ($Bi_2Mo_3O_{12}$) catalyst and 60 to 99 wt % of the γ-bismuth molybdate ($Bi_2MoO_6$) catalyst.

8. The method according to claim 7, wherein the ratio of the atomic number of bismuth/molybdenum is adjusted to a range from 0.1 to 2, and the pH of the mixed solution is controlled to a range from 0.1 to 5, in step a) for obtaining the α-bismuth molybdate ($Bi_2Mo_3O_{12}$).

9. The method according to claim 7, wherein the ratio of the atomic number of bismuth/molybdenum is adjusted to a range from 1 to 3, and the pH of the mixed solution is controlled to a range from 0.1 to 10, in step a) for obtaining the γ-bismuth molybdate ($Bi_2MoO_6$).

10. The method according to claim 3, wherein the C4 mixture comprises 0.5 to 50 wt % of n-butane, 40 to 99 wt % of n-butene, and 0.5 to 10 wt % of another C4 mixture.

* * * * *